US012620490B2

(12) United States Patent
Ghose et al.

(10) Patent No.: US 12,620,490 B2
(45) Date of Patent: May 5, 2026

(54) SYSTEM AND METHOD FOR DETECTING RECURRENCE OF A DISEASE

(71) Applicants:GE Precision Healthcare LLC, Wauwatosa, WI (US); The Trustees of Indiana University, Bloomington, IN (US)

(72) Inventors: Soumya Ghose, Niskayuna, NY (US); Fiona Ginty, Saratoga Springs, NY (US); Cynthia Elizabeth Landberg Davis, Niskayuna, NY (US); Sanghee Cho, Niskayuna, NY (US); Sunil S. Badve, Indianapolis, IN (US); Yesim Gokmen-Polar, Noblesville, IN (US)

(73) Assignees: GE Precision Healthcare LLC, Wauwatosa, WI (US); The Trustees of Indiana University, Bloomington, IN (US)

( * ) Notice: Subject to any disclaimer, the term of this patent is extended or adjusted under 35 U.S.C. 154(b) by 433 days.

(21) Appl. No.: 17/704,531

(22) Filed: Mar. 25, 2022

(65) Prior Publication Data

US 2023/0307137 A1 Sep. 28, 2023

(51) Int. Cl.
| | |
|---|---|
| *G16H 50/30* | (2018.01) |
| *G06T 7/00* | (2017.01) |
| *G06V 10/26* | (2022.01) |
| *G16H 30/40* | (2018.01) |

(52) U.S. Cl.
CPC ........... *G16H 50/30* (2018.01); *G06T 7/0012* (2013.01); *G06V 10/26* (2022.01); *G16H 30/40* (2018.01); *G06T 2207/30096* (2013.01)

(58) Field of Classification Search
CPC ...... G16H 50/30; G16H 30/40; G06T 7/0012; G06T 2207/30096; G06T 2207/10072; G06T 2207/10116; G06T 2207/10132; G06T 2207/20081; G06T 2207/20084; G06T 2207/30068; G06T 7/11; G06T 7/13; G06T 2207/20104; G06V 10/26; G06V 10/764; G06N 3/08; G06N 20/00
See application file for complete search history.

(56) References Cited

U.S. PATENT DOCUMENTS

| | | | |
|---|---|---|---|
| 10,380,739 B2 | 8/2019 | Vega | |
| 11,721,427 B2 * | 8/2023 | Barnes | ................. G06V 20/695 |
| 11,990,241 B2 * | 5/2024 | Yan | ........................... G06T 7/00 |

(Continued)

FOREIGN PATENT DOCUMENTS

CN 110400287 * 9/2021

OTHER PUBLICATIONS

La Forgia, Daniele, et al. "Radiomic analysis in contrast-enhanced spectral mammography for predicting breast cancer histological outcome." Diagnostics 10.9 (2020): 708. (Year: 2020).*

(Continued)

*Primary Examiner* — Andrae S Allison

(57) ABSTRACT

A method for determining a recurrence of a disease in a patient includes generating a medical image of an organ of the patient and then extracting an invasive edge around an area of interest in the medical image. A plurality of radiomics features is obtained from the invasive edge and the recurrence of the disease is determined based on the plurality of radiomics features.

16 Claims, 5 Drawing Sheets

(56) References Cited

U.S. PATENT DOCUMENTS

| | | | |
|---|---|---|---|
| 2017/0193657 A1* | 7/2017 | Madabhushi | G06F 18/24317 |
| 2018/0247410 A1* | 8/2018 | Madabhushi | A61B 5/7267 |
| 2019/0087532 A1* | 3/2019 | Madabhushi | G06V 30/19173 |
| 2020/0234442 A1* | 7/2020 | Barnes | C12Q 1/6886 |
| 2021/0233236 A1* | 7/2021 | Dogdas | G06T 7/0012 |
| 2022/0130084 A1* | 4/2022 | Litwiller | G06V 10/26 |
| 2022/0261668 A1* | 8/2022 | Stumpe | G06N 3/045 |
| 2023/0309836 A1* | 10/2023 | Ghose | G06V 20/698 |
| | | | 382/128 |
| 2023/0317293 A1* | 10/2023 | Cho | G16H 30/00 |
| | | | 382/100 |

OTHER PUBLICATIONS

Berthel et al, Detailed resolution analysis reveals spatial T cell heterogeneity in the invasive marginof colorectal cancer liver metastases associated with improved survival, Oncoimmunology2017, vol. 6, No. 3, e1286436 (10 pages) (Year: 2017).*

Hendry et al, Assessing Tumor-infiltrating Lymphocytes in Solid Tumors, Advances in Anatomic Pathology • Aug. 2017 (Year: 2017).*

Xu et al, Radiomic analysis of contrast-enhanced CT predictsmicrovascular invasion, Journal of Hepatology 2019 vol. 70 j 1133-1144 (Year: 2017).*

Koelzer et al, The tumor border configuration of colorectal cancer, FrontiersinOncology | Gastrointestinal Cancers Feb. 2014 vol. 4 Article29 | 4 (Year: 2014).*

Algohary et al., "Combination of Peri-Tumoral and Intra-Tumoral Radiomic Features on Bi-Parametric MRI Accurately Stratifies Prostate Cancer Risk: A Multi-Site Study." Cancers vol. 12,8 2020, 13 pages.

Beig et al., "Perinodular and Intranodular Radiomic Features on Lung CT Images Distinguish Adenocarcinomas from Granulomas." Radiology vol. 290,3 (2019): 783-792, 10 pages.

Braman et al., "Association of Peritumoral Radiomics With Tumor Biology and Pathologic Response to Preoperative Targeted Therapy for HER2 (ERBB2)-Positive Breast Cancer." JAMA network open vol. 2,4 e192561. Apr. 5, 2019, 18 pages.

Braman et al., "Intratumoral and peritumoral radiomics for the pretreatment prediction of pathological complete response to neoadjuvant chemotherapy based on breast DCE-MRI." Breast cancer research : BCR vol. 19,1 57. May 18, 2017, 14 pages.

Hendry et al., "Assessing Tumor-infiltrating Lymphocytes in Solid Tumors: A Practical Review for Pathologists and Proposal for a Standardized Method From the International Immunooncology Biomarkers Working Group: Part 1: Assessing the Host Immune Response, TILs in Invasive Breast Carcinoma and Ductal Carcinoma In Situ, Metastatic Tumor Deposits and Areas for Further Research." Advances in anatomic pathology vol. 24,5 (2017): 235-251, 32 pages.

Prasanna et al., "Radiomic features from the peritumoral brain parenchyma on treatment-naïve multi-parametric MR imaging predict long versus short-term survival in glioblastoma multiforme: Preliminary findings." European radiology vol. 27,10 (2017): 4188-4197, 20 pages.

Bera Kaustav et al: "Predicting cancer outcomes with radiomics and artificial intelligence in radiology", Nature Reviews Clinical Oncology, Nature, NY, US, vol. 19, No. 2, Oct. 18, 2021 (Oct. 18, 2021), pp. 132-146, XP037675447.

Chong Huan-Huan et al: "Multi-scale and multi-parametric radiomics of gadoxetate disodium-enhanced MRI predicts microvascular invasion and outcome in patients with solitary hepatocellular carcinoma= 5 cm", European Radiology, Springer Berlin Heidelberg, Berlin/Heidelberg, vol. 31, No. 7, Jan. 14, 2021 (Jan. 14, 2021), pp. 4824-4838, XP037484350.

EP application 23161412.4 filed Mar. 13, 2023—extended Search Report issued Aug. 14, 2023; 13 pages.

Groendahl A Rosvoll et al: "PO-0967 Prediction of treatment outcome for head and neck cancers using radiomics of PET/CT images", Radiotherapy and Oncology, vol. 133, XP085697738.

Holbrook Matthew D. et al: "MRI-based radiomics of sarcomas in the preclinical arm of a co-clinical trial", Medical Imaging 2020: Biomedical Applications in Molecular, Structural, and Functional Imaging, Feb. 28, 2020 (Feb. 28, 2020), XP093070806.

Lee S. et al: "1219P AI-powered prediction of 2-year relapse-free survival in operable NSCLC patients using beritumoral radiomic features according to tumour size in chest CT images", Annals of Oncology, vol. 31, Sep. 1, 2020 (Sep. 1, 2020), p. S796, XP093070807.

Mayerhoefer Marius E. et al: "Introduction to Radiomics", The Journal of Nuclear Medicine, vol. 61, No. 4, Apr. 1, 2020 (Apr. 1, 2020), pp. 488-495, XP093070810.

Mouraviev Andrei et al: "Use of radiomics for the prediction of local control of brain metastases after stereotactic radiosurgery", NeuroOncology, vol. 22, No. 6, Jun. 9, 2020 (Jun. 9, 2020), pp. 797-805, XP093070802.

* cited by examiner

202

204

206

208

214 210 212

400

SYSTEM AND METHOD FOR DETECTING RECURRENCE OF A DISEASE

FIELD

Embodiments of the subject matter disclosed herein relate to medical imaging, and more particularly to breast cancer detection using medical imaging.

BACKGROUND

Breast cancer is the most common cancer in women worldwide, affecting an estimated 1.5 million women around the world each year. It is also a leading cause of cancer-related death in women. Early detection of breast cancer can reduce mortality and the intensity of treatment required. Among the breast cancer subtypes, Triple negative breast cancer (TNBC) is the most aggressive and heterogeneous breast cancer subtype and accounts for 10-20% of newly diagnosed early breast cancers. The lack of hormone receptors and human epidermal growth factor receptor 2 (HER2) prevent TNBCs from being treated with therapies against these targets. Recurrences of TNBC occurs in about 25% of patients and is observed within the first few years after diagnosis. Early detection of recurrence from routinely collected mammograms would allow early intervention and a better treatment procedure.

In many cases, the cancer tumor in a breast is detected by a medical imaging procedure such as a Mammography. In digital mammography, a scout or pre-shot image may be taken of a patient to determine an x-ray technique (e.g., x-ray tube current and voltage, exposure time) to acquire images of the patient having a sufficient brightness. Upon determination of the x-ray technique, one or more x-ray images of the patient may be acquired. In some examples, multiple x-ray images may be acquired at different view angles and/or at different energy levels.

Although, an existing cancer tumor may be detected using the mammography technique, predicting recurrence in TNBC is difficult from routinely collected clinical data including biopsy samples, clinical information, and mammograms. Therefore, there is a need for an improved system and method to determine recurrence for triple negative breast cancer patients.

BRIEF DESCRIPTION

In accordance with an embodiment of the present technique, a method for determining a recurrence of a disease in a patient is presented. The method includes generating a medical image of an organ of the patient and extracting an invasive edge around an area of interest in the medical image. The method further includes obtaining a plurality of radiomics features from the invasive edge. Finally, the method includes determining the recurrence of the disease based on the plurality of radiomics features.

In accordance with another embodiment of the present technique, a system including a memory storing a machine learning model is presented. The system further includes a display device and a processor that is communicably coupled to the memory and configured to receive a medical image of an organ of the patient. The processor is further configured to classify the medical image using the machine learning model network as a disease recurrent image or a disease non-recurrent image based on the radiomics features of an invasive edge around an area of interest in the medical image and display the disease recurrent image via the display device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

One or more specific embodiments of the present disclosure are described below. These described embodiments are only examples of the systems and methods for locally enhancing a medical image. The skilled artisan will understand that specific details described in the embodiments can be modified when being placed into practice without deviating from the spirit of the present disclosure.

As used herein, an element or step recited in the singular and proceeded with the word "a" or "an" should be understood as not excluding plural of said elements or steps, unless such exclusion is explicitly stated. Moreover, the terms "first," "second," and "third," etc. are used merely as labels, and are not intended to impose numerical requirements or a particular positional order on their objects. Furthermore, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." As the terms "connected to," "coupled to," etc. are used herein, one object (i.e., a material, element, structure, number, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

Further, while the embodiments disclosed herein are described with respect to a mammography apparatus for the 2-dimensional imaging of breast tissue, it is to be understood that embodiments of the invention may be applicable to other types of imaging devices for both 2-dimensional (2D) and 3-dimensional (3D) imaging including, for example, digital breast tomosynthesis (DBT) and spectral mammography (single or multi-energy), X-ray imaging, Automated Breast Ultrasound (ABUS) imaging, magnetic resonance imaging (MRI), computed tomography (CT) as well as for imaging procedures for tissue other than breast tissue. Further still, embodiments of the invention may be used to analyze tissue, generally, and are not limited to analyzing human tissue.

The malignancy of breast cancer is unclear and no dominant cause has emerged; however, early detection and treatment may generate a good prognosis for the patient. Currently, X-ray mammography is an important factor in early detection and can greatly reduce the number of deaths caused by breast cancer.

Figure 1:
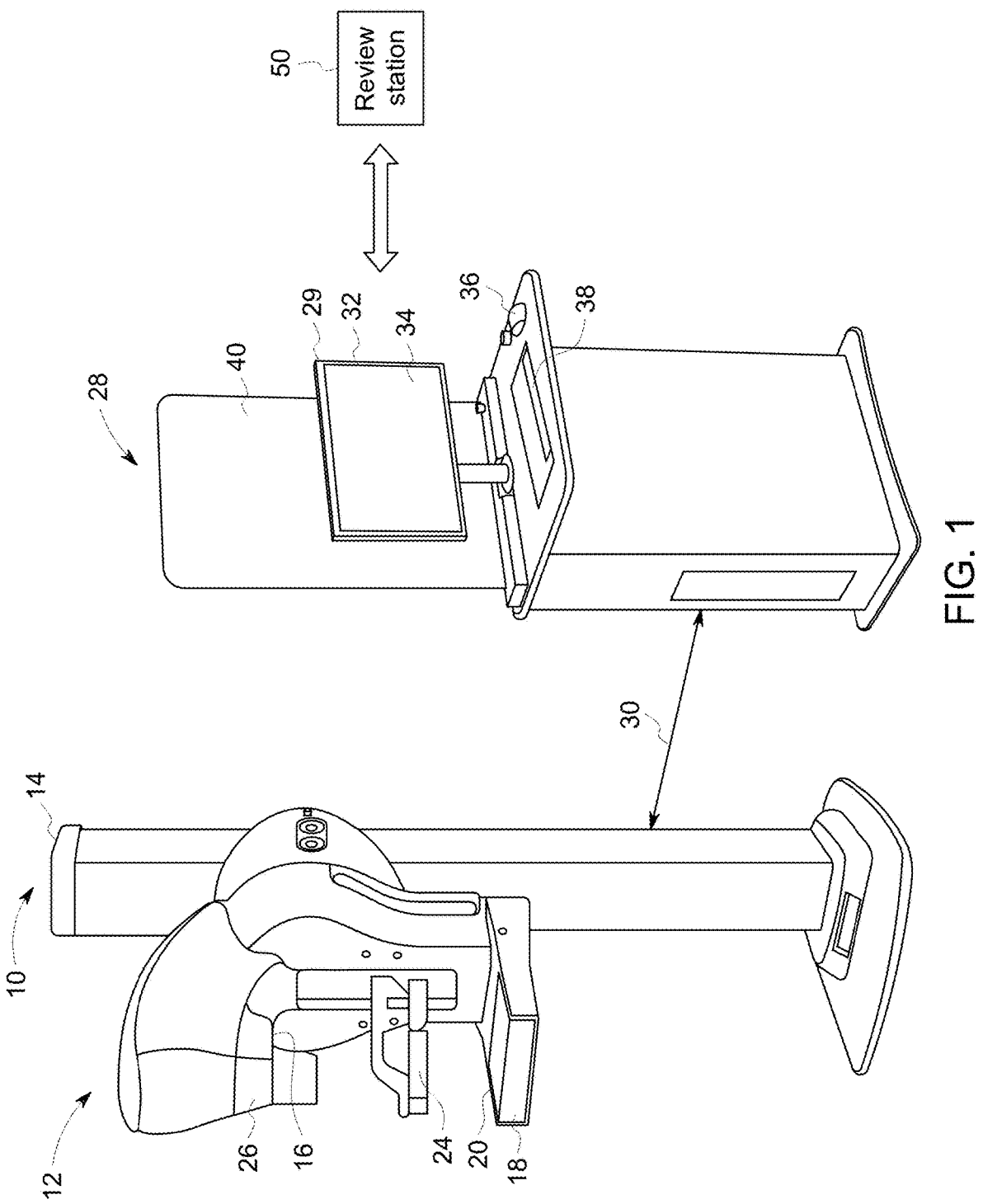
FIG. 1 is a schematic illustration of an exemplary x-ray system, in accordance with an embodiment of the present technique.

Referring to FIG. 1, an image of an exemplary x-ray system is shown. The x-ray system 10 includes an x-ray apparatus 12. The x-ray apparatus 12 may be a tomosynthesis apparatus, such as the digital breast tomosynthesis ("DBT") apparatus shown in FIG. 1. Though reference is made herein to breast biopsies and DBT, it is to be understood that the systems and methods described herein may be applied to other similar uses in the field of x-ray imaging and tomography, and is not limited to the field of DBT or breast biopsies.

The x-ray apparatus 12 includes a support structure 14, to which an x-ray source 16 and an x-ray detector 18 may be attached. The x-ray source 16 is directed toward a volume or object 22 to be x-rayed, and is configured to emit a beam of x-rays at desired times and to acquire one or more x-ray images 42. Once the x-rays are emitted, the beam of x-rays pass through the object 22 and are picked up by or hit the detector 18. The detector 18 may be any one of a variety of different detectors conventionally known in the art or that will become available in the future, such as an x-ray detector, digital radiography detector, or flat panel detector.

The x-ray apparatus 12 may also include an object support 20 on which the object 22 is placed. The object 22 may be a portion of a patient, such as a breast. The x-ray apparatus 12 may further include compression means, such as a compression paddle 24, which compresses the object 22. Compression paddle 24 holds the breast still and in place while optionally providing apertures to allow for insertion of a biopsy tool, needle, core needle, or vacuum assisted core needle. Compression paddle 24 also serves to compress the object or breast to minimize the thickness traversed by the x-rays and to help reduce movement of the object 22 due to the patient moving. Optionally, the x-ray apparatus 12 may also include a patient shield 26 to shield portions of a patient from radiation exposure from the x-ray source and/or to shield the patient from viewing the procedure and biopsy tissue samples.

In addition to the x-ray apparatus 12, the x-ray system 10 may include a work station 28, which includes a computer or controller 29. The work station 28 and/or controller 29 is connected or in communication with at least the x-ray apparatus 12, through connection 30, which could be wired or wireless. The controller 29 may also be connected to a display 32 comprising an interface 34, which allows a user to interact with the controller 29 to acquire x-ray images, position and operate parts of the x-ray apparatus 12, define or propose a region of interest or field of view, and display images 42. The controller 29, which may be a processor, computer, etc., may include a memory or storage and processing circuitry that executes stored program logic and may be any one of a different computers, processors, controllers, or combination thereof that are available for and compatible with the various types of equipment and devices used in the x-ray system 10.

Through its processors and controllers, the controller 29 controls the operation and function of the x-ray source 16 and the detector 18. The controller 29 is capable of controlling when the x-ray source 16 emits x-rays, how the detector 18 reads and conveys information or signals after the x-rays hit the detector 18, and how the x-ray source 16 and the detector 18 moves relative to one another and relative to the object 22. The controller 29 also controls how information, including images 42 and data acquired during the operation, is processed, displayed, stored, and manipulated. The different processing steps performed by the controller 29 are dictated and controlled by software designed to allow controller 29 to perform the various operations underlying the acquisition of x-rays, some of which are discussed herein. Information may also be stored in one or more memories of controller 29 for later retrieval and use.

The work station 28 typically includes one or more of the display 32 with the interface 34, selecting means 36, input means 38, and a radiation shield 40. The work station 28 can be used by an x-ray technician, physician, or other trained professional for interacting with the x-ray apparatus 12 as a user. The input means 38 may be a mouse, keyboard, touch pad, or other input devices. The display 32 can display one or more images 42 at the same time, different times, in sequence, or out of sequence that were acquired during an x-ray procedure, or track data relevant to the x-ray system 10 from controller 29. The display coupled to the workstation 28 may be utilized to observe the images 42 and to control scout image acquisition, further image acquisition, which may be used for imaging of biopsy samples, for example. It should be noted that the images generated by system 10 may be further analyzed at a review station 50 which may be located at a remote place or may be on a cloud. The review station 50 may include a set of tools to help manage large amounts of data, quickly explore precise, detailed medical images and help make a quick and accurate diagnosis. For example, in one embodiment, the review station may predict a recurrence of disease as will be explained in more detail below. One example of such a review station is General Electric (GE) Healthcare's Seno Iris™ review station.

As explained earlier, among the breast cancer subtypes, Triple negative breast cancer (TNBC) is the most aggressive and heterogeneous breast cancer subtype. In accordance with one embodiment of the present technique, radiomics features extracted from invasive edge (or propagating front) of breast tumors as observed in routine mammograms from system 10 are used for predicting recurrence in TNBC patients. In general, the invasive edge includes clusters of invasive cells with motile characteristics suggesting dynamic interaction between the stroma and the tumor cells and represents the beginning of the invasion and metastatic processes. For example, irregular infiltration of the surrounding normal tissue could be detected in the form of greater heterogeneity in intensity distribution by radiomic methods. In one embodiment, an area in the tumor region is also extracted along with the invasive edge around the tumor region and the recurrence of the disease is determined based on the radiomics features in both the invasive edge and the tumor region area.

Figure 2:
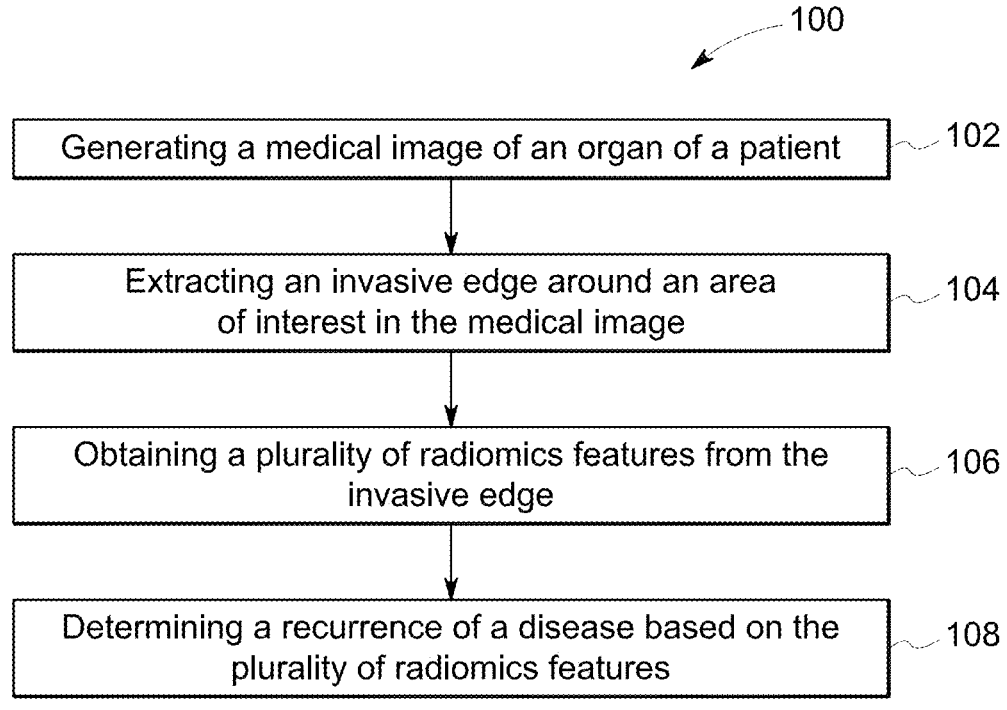
FIG. 2 is a flowchart representing a method for detecting a recurrence of a disease from medical images, in accordance with an embodiment of the present technique.

FIG. 2 shows flowchart representing a method 100 for detecting recurrence of a disease such as TNBC from medical images. In one embodiment, the method may be implemented by review station 100 in coordination with an imaging system such as x-ray system 10. At step 102, the method 100 includes generating a medical image of an organ of a patient at step 102. The medical image may be an x-ray image generated by a system such as x-ray system 10 of FIG. 1. However, in other embodiments, the medical image may be a computed tomography (CT) image or magnetic resonance image (MRI), for example.

At step 104, the method includes extracting an invasive edge around an area of interest in the medical image. For example, the area of interest may be a tumor region which may be manually or automatically segmented from the medical image. The invasive edge then may be determined by extracting a peritumoral region from the area of interest. The invasive edge that is extracted may be a thick edge having a width. The width dimension depends on nature of a particular disease that is being predicted and the image resolution, for example. The width dimension may be in the range of 0.5 mm to 1 cm. For example, in one embodiment, the invasive edge may be an area around the tumor region (excluding the tumor region itself) having a width of 1 mm. In one embodiment, the invasive edge may be extracted automatically by using a deep learning network. The deep learning network may be trained based on past image data (e.g., mammograms) of a number of patients. The past image data may be collected over a number of years (e.g., 5 years) in the past. In another embodiment, the invasive edge may be extracted manually from the medical image.

Figure 3A:
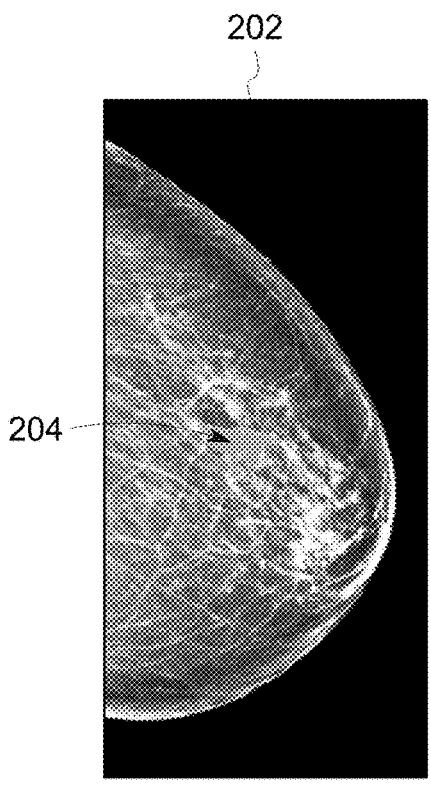
FIGS. 3A and 3B are pictorial views showing extraction of an invasive edge around an area of interest in the medical image, in accordance with an embodiment of the present technique.
Figure 3B:

FIGS. 3A and 3B show extraction of an invasive edge around an area of interest in the medical image, in accordance with an embodiment of the present technique. Specifically, FIG. 3A shows a first medical image 202 of a breast having a tumor 204. The medical image may be a routine mammogram obtained using the x-ray system 10, for example. FIG. 3B is a second medical image 206 showing an invasive edge 208 around the tumor 204. The invasive edge has a width of 1 mm.

Figure 3C:
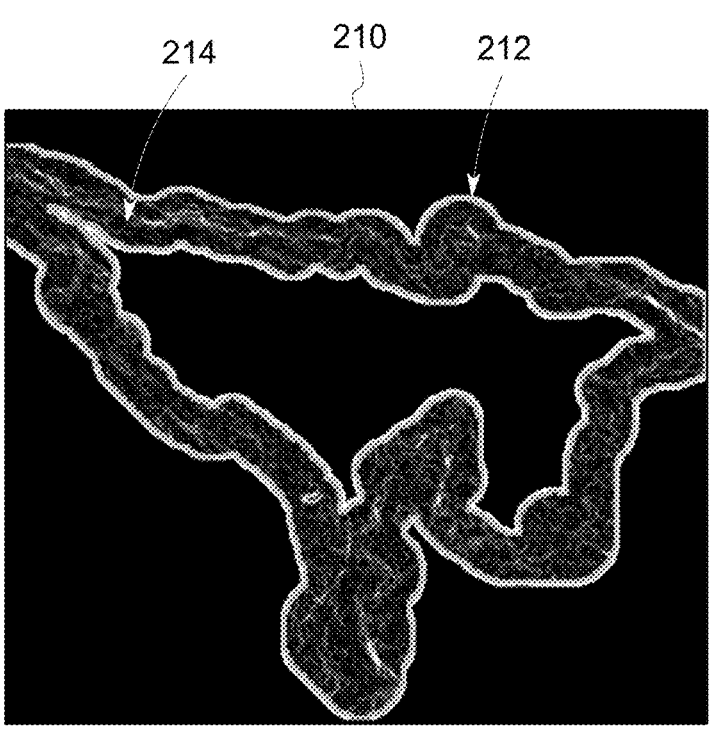
FIG. 3C is a pictorial view of an image of the extracted invasive edge from the medical image, in accordance with an embodiment of the present technique.

FIG. 3C depicts an image 210 of the extracted invasive edge 212 from the medical image 202. The invasive edge 212 includes a plurality of radiomics features such as gradient and texture features that depicts tumor heterogeneity 214. In accordance with an embodiment of the present technique, based on the tumor heterogeneity 214, recurrence for TNBC is predicted.

Referring back to FIG. 2, at step 106, the method 100 includes obtaining a plurality of radiomics features from the invasive edge extracted around the area of interest. The radiomics features may include shape, texture, intensity, and gradient magnitude or combinations thereof, for example. The radiomics features further may include mean, median, skewness, kurtosis, standard deviation for shape, texture, intensity and gradient. Moreover, the radiomics feature may include Sobel and Canny features for gradient, and Haralick feature for texture. Finally, at step 108, a recurrence of a disease for the patient is determined based on the plurality of radiomics features. The disease may be a triple negative breast cancer as described earlier or may be other breast cancer types such as receptor positive and HER-2 positive or other cancers including prostate, lung colon, liver and glioblastoma.

It should be noted that, there can be thousands of radiomics features present in the invasive edge and analyzing all the features may not be an efficient way to determine recurrence of a disease. Therefore, in one embodiment, the step of determining the recurrence of the disease includes using a machine learning model to reduce the number of radiomics features. In other words, only a small number of radiomics features that are significant for determining recurrence of a disease are selected from the plurality of radiomics features. In one embodiment, the number of significant radiomics features may be automatically determined using a machine learning model which may include a non-linear random forest classifier. Examples of significant radiomics features may be statistics (mean, median, mode, standard deviation, skewness and kurtosis) of gradient magnitude of image pixels. Magnitude of gradient may be a good feature for recurrence prediction of the disease.

The step 108 of predicting recurrence further includes using the machine learning model trained on the significant radiomics features that have been selected to predict the recurrence of the disease. The machine learning model may be a random forest classifier or a deep neural network. For example, in one embodiment, the random forest classifier determines the significant radiomics features as well as predicts the recurrence from the radiomics features. In one embodiment, the random forest classifier may be trained using a training data set of a plurality of radiomics features of the invasive edges of various patients. The training data set may include radiomics features of invasive edges of patients having the disease as well as patients not having the disease. Once the random forest classifier is trained and validated, the same is then used for determining a recurrence of a disease in a current patient based on input radiomics features that are fed to the classifier. In another embodiment, the random forest classifier determines the significant radiomics features and then a deep neural network predicts the recurrence from the radiomics features. In such an embodiment, the deep neural network is trained using a training data set of a plurality of radiomics features of the invasive edges of various patients. It yet another embodiment, the machine learning model may be trained directly trained on the invasive edge images themselves (without extracting the radiomic features) to predict recurrence of the disease.

Figure 4:
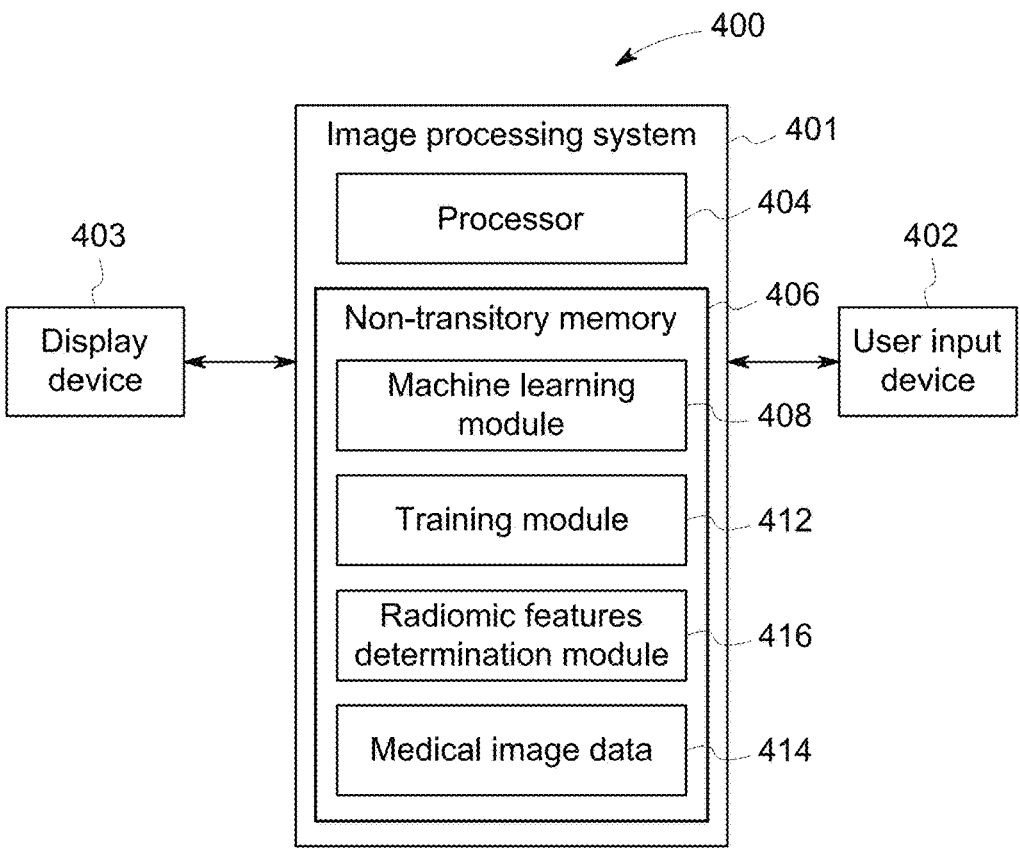
FIG. 4 is a schematic diagram illustrating an image processing system for detecting a recurrence of a disease using a deep neural network, according to an exemplary embodiment.

Referring to FIG. 4, a medical image processing system 400 is shown, in accordance with an exemplary embodiment. In some embodiments, the medical image processing system 100 is disposed at the review station 50 of FIG. 1 which can receive images from the medical imaging system or from a storage device which stores the images generated by the medical imaging system. In some embodiments, the medical image processing system 400 is disposed at a device (e.g., edge device, server, etc.) communicably coupled to the review station via wired and/or wireless connections. The medical image processing system 400 may comprise image processing system 401, user input device 402, and display device 403.

Image processing system 401 includes a processor 404 configured to execute machine readable instructions stored in non-transitory memory 406. Processor 404 may be single core or multi-core, and the programs executed thereon may be configured for parallel or distributed processing. In some embodiments, the processor 404 may optionally include individual components that are distributed throughout two or more devices, which may be remotely located and/or configured for coordinated processing. In some embodiments, one or more aspects of the processor 404 may be virtualized and executed by remotely-accessible networked computing devices configured in a cloud computing configuration.

Non-transitory memory 406 may store machine learning module 408, radiomics feature determination module 416, training module 412, and medical image data 414. Machine learning module 408 may include one or more classifiers and/or deep neural networks, comprising a plurality of parameters (including weights, biases, activation functions), and instructions for implementing the one or more classifiers and/or deep neural networks to receive radiomics features and map the radiomics features to output, wherein a classification of recurrence or non-recurrence of the disease corresponding to the radiomics features may be produced from the output. For example, Machine learning module 408 may store instructions for implementing a random forest classifier or a neural network, such as the convolutional neural network (CNN). However, other architectures such as combinations of fully connected networks and CNNs or generative adversarial networks and their variants can be used as well.

Machine learning module 408 may include trained and/or untrained classifiers/neural networks and may further include various data, or tags pertaining to the one or more neural networks stored therein. In some embodiments, the deep neural network tags may include an indication of the training data used to train a deep neural network, a training method employed to train the deep neural network, an accuracy/validation score of the deep neural network, and a type of anatomy/imaging protocol for which the deep neural network may be applied.

Non-transitory memory 406 further stores radiomics feature determination module 416. Radiomics feature determination module 416 may include instructions that, when executed by processor 404, cause image processing system 401 to conduct one or more of the steps of method 100, discussed above with respect to FIG. 2. In some embodiments, radiomics feature determination module 416 includes instructions for extracting an invasive edge around an area of interest in the medical image 414, obtaining a plurality of radiomic features from the invasive edge and finally, ranking a significant radiomic features which are most predictive of a recurrence disease and selecting those significant radiomic feature to be fed to the machine learning module 408 as an input. In one embodiment, radiomics feature determination module 416 may itself include another deep neural network for extracting the invasive edge around the area of interest.

Non-transitory memory 406 may further store training module 412, which comprises instructions for training one or more of the machine learning models stored in machine learning module 408. Training module 412 may include instructions that, when executed by processor 404, cause image processing system 401 to conduct one or more of the steps of method 100, discussed above with respect to FIG. 2. In some embodiments, training module 412 includes instructions for implementing one or more gradient descent algorithms, applying one or more loss functions, and/or training routines, for use in adjusting parameters of one or more deep neural networks of machine learning module 408. In some embodiments, training module 412 includes instructions for generating training data pairs from medical image data 414. In some embodiments, training data pairs comprise corresponding pairs of radiomics feature set and corresponding disease status of a patient. In some embodiments, the training module 412 is not disposed at the image processing system 401 but located at a remote location. The machine learning module 408 includes trained and validated network(s).

Non-transitory memory 406 further stores medical image data 414. Medical image data 114 includes for example, X-ray images acquired using X-ray or CT system, MR images acquired using an MRI system, ultrasound images acquired by an ultrasound system, etc. For example, the medical image data 114 may store noisy and/or pristine medical images. In some embodiments, medical image data 114 may include a plurality of training data pairs comprising pairs of noisy and pristine medical images.

In some embodiments, the non-transitory memory 406 may include components disposed at two or more devices, which may be remotely located and/or configured for coordinated processing. In some embodiments, one or more aspects of the non-transitory memory 406 may include remotely-accessible networked storage devices configured in a cloud computing configuration.

Image processing system 400 may further include user input device 402. User input device 402 may comprise one or more of a touchscreen, a keyboard, a mouse, a trackpad, a motion sensing camera, or other device configured to enable a user to interact with and manipulate data within image processing system 401. As an example, user input device 402 may enable a user to make a classification of a medical image as training data, validation data or the real time data that needs to be analyzed for recurrence of the disease.

Display device 403 may include one or more display devices utilizing virtually any type of technology. In some embodiments, display device 403 may comprise a computer monitor, and may display unprocessed and processed medical images and/or parametric maps. Display device 403 may be combined with processor 404, non-transitory memory 406, and/or user input device 402 in a shared enclosure, or may be peripheral display devices and may comprise a monitor, touchscreen, projector, or other display device known in the art, which may enable a user to view medical images, and/or interact with various data stored in non-transitory memory 406.

It should be understood that image processing system 400 shown in FIG. 4 is for illustration, not for limitation. Another appropriate image processing system may include more, fewer, or different components.

Figure 5A:
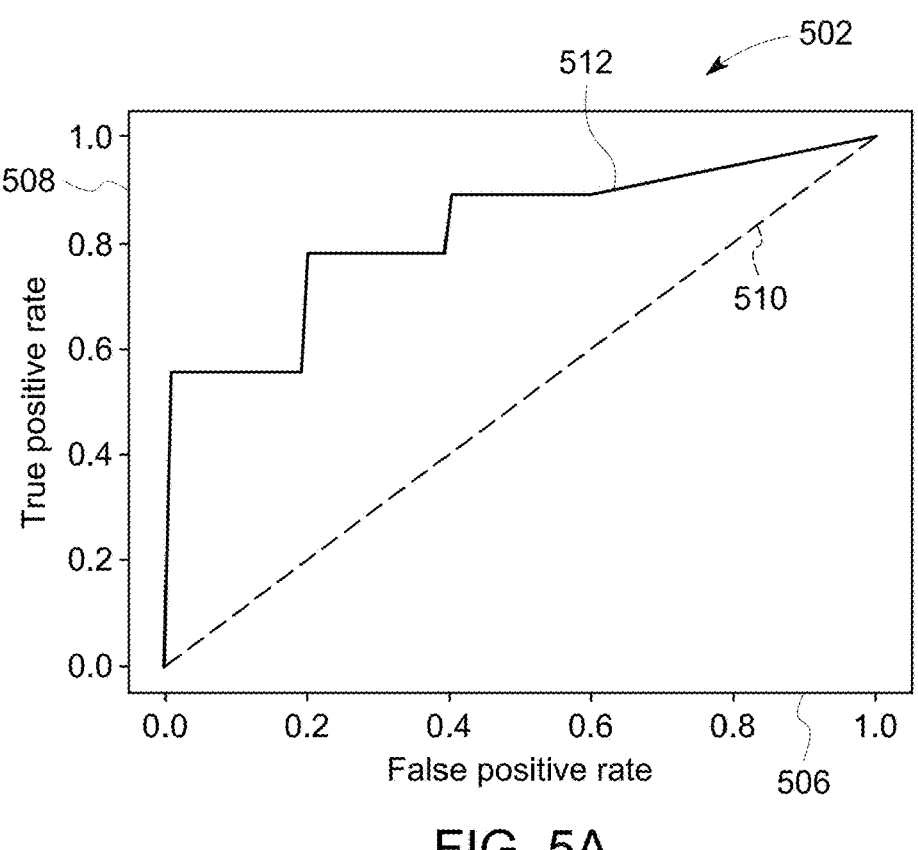
FIGS. 5A and 5B are pictorial views showing validation results of an experimental study for peritumoral region and intra-tumoral region, in accordance with an embodiment of the present technique
Figure 5B:
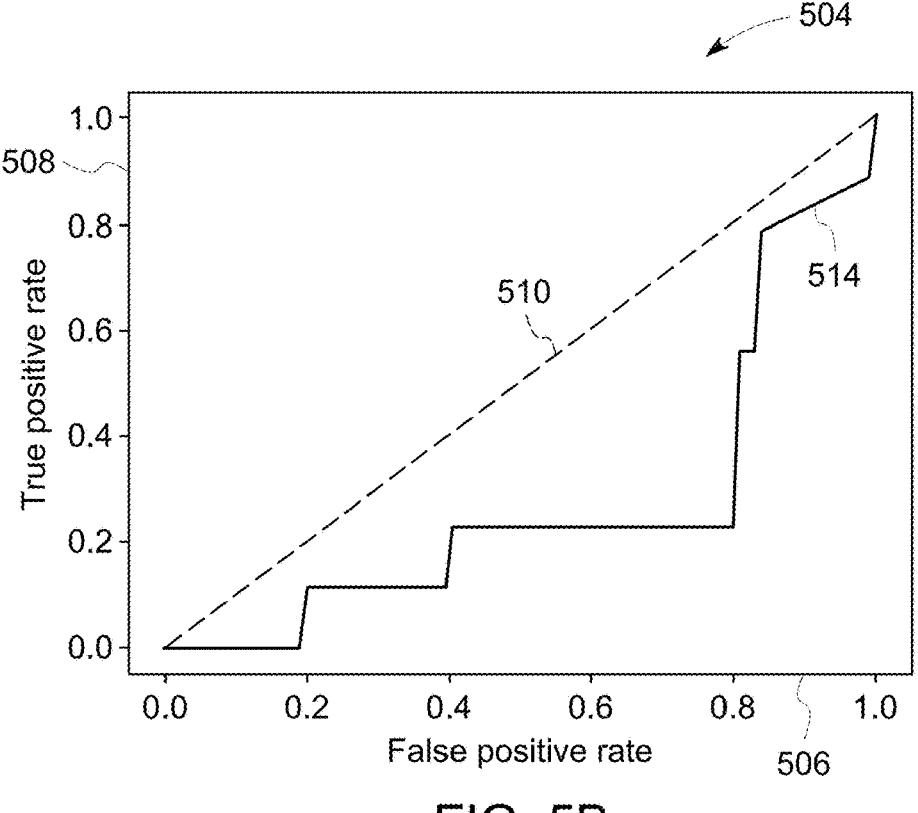

To validate the results of the present technique, an experimental study was conducted to train and build a machine learning model such as the machine learning module 408 for the invasive edge radiomics features analysis. The study was then compared with similar machine learning model built for analysis of radiomics features in the tumor area. In a cohort of 29 patients with 5-year outcomes, manually segmented breast lesions in mammograms were used to automatically determine the invasive edge of the breast tumor. A width of 1 mm from both intra-tumoral (i.e., invasive edge) and peritumoral region (i.e., within the tumor area) was used to automatically identify the invasive edge. FIGS. 5A and 5B show the validation results of this experimental study for peritumoral region and intra-tumoral region respectively. Over 2000 radiomics features from the invasive edge and the central regions of the tumor were extracted for this study and then were ranked to analyze only a significant number of radiomics features for determining the recurrence of the disease. Specifically, FIG. 5A shows a first plot 502 depicting ability of the machine learning module 408 to correctly determine a recurrence of a disease in a patient based on the radiomics features in the peritumoral region. Similarly, FIG. 5B shows a second plot 504 depicting ability of the machine learning module 408 to correctly determine a recurrence of a disease in a patient based on the radiomics features in the intra-tumoral region.

In both FIGS. 5A and 5B, a horizontal axis 506 represents false positive rate and a vertical axis 508 represents a true positive rate. In plot 502, a first receiver operating characteristic (ROC) curve 512 is shown which represents results of prediction of recurrence of the disease based on the radiomics features in the invasive edge. Similarly, in plot 504, a second ROC curve 514 is shown which represents results of prediction of recurrence of the disease based on the radiomics features in the tumoral region. Two significant radiomic features, skewness and kurtosis of continuous gradient magnitude, were used for used for this purpose. The ROC curves 512 and 514 for peritumoral and intra-tumoral region respectively are plotted by varying a threshold value of selected radiomic feature above which the image will be classified as disease recurrent image and below which the image will be classified as a disease non-recurrent image. For example, if coordinates of a point on the ROC curve are (0,1) i.e., false positive rate 0 and true positive rate 1, then it means all samples were correctly classified as positive cases (i.e., disease recurrence images). On the contrary, if coordinates of a point on the ROC curve are (1,0) i.e., false positive rate 1 and true positive rate 0, then it means all samples were incorrectly classified as negative cases (i.e., disease non-recurrent images).

A dotted line between the two coordinates (0,1) and (1,0) is a random classifier line 510. Coordinates above the random classifier line 510 represent good classification results (better than random); points below the line represent bad results (worse than random). As can be seen from plots 502 and 504, the ROC curve 512 for the radiomic feature of peritumoral region has all the coordinates above the random classifier line 510 whereas the ROC curve 514 for the radiomic feature of intra-tumor region has all the coordinates below the random classifier line 510. Thus, it can be seen that the performance of the ROC curve 512 is much better when compared with ROC curve 514.

One of the advantages of the present technique is that heterogeneity features extracted from the invasive edge has a better predictive accuracy compared to heterogeneity features extracted from entire tumor. Further, the technique can be used for cancer risk stratification for other cancers including prostate, colon, lung, liver and glioblastoma. Moreover, the technique could be readily exported into 3D and in other imaging modalities including CT, MRI and ultrasound. Moreover, the technique works well with routinely collected imaging data like mammograms.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter set forth herein without departing from its scope. While the dimensions and types of materials described herein are intended to define the parameters of the disclosed subject matter, they are by no means limiting and are exemplary embodiments. Many other embodiments will be apparent to those of skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for determining a recurrence of a disease in a patient, the method comprising:
    generating a medical image of an organ of the patient;
    extracting an invasive edge around an area of interest in the medical image;
    obtaining a plurality of radiomics features from the invasive edge; and
    determining the recurrence of the disease based on the plurality of radiomics features,
    wherein the disease defines a breast cancer,
    wherein determining the recurrence of the disease comprises:
        ranking the plurality of radiomics features based on their ability to predict the recurrence of the cancer using a machine learning classifier; and
        providing high ranking radiomics features to a deep neural network for classifying the medical image as a disease recurrent medical image or a disease non-recurrent medical image, and
    wherein the deep neural network is trained on radiomics features that have been selected to predict the recurrence of the disease based on a plurality of training data pairs comprising noisy and pristine medical images.

2. The method of claim 1, wherein the medical image comprises an X-ray image, a computed tomography (CT) image, a magnetic resonance image (MRI) or an ultrasound image.

3. The method of claim 1, wherein the area of interest includes a tumor region.

4. The method of claim 1, wherein extracting the invasive edge comprises segmenting the area of interest from the medical image.

5. The method of claim 4, wherein the invasive edge includes an edge surrounding the area of interest having a width.

6. The method of claim 5, wherein the width of the invasive edge is dependent on the nature of the disease and a resolution of the medical image.

7. The method of claim 5, wherein the width of the invasive edge is in the range of 0.5 mm to 1 cm.

8. The method of claim 1, wherein the plurality of radiomics features comprises shape, texture, intensity, and gradient magnitude of the invasive edge.

9. The method of claim 1, wherein the disease comprises triple negative breast cancer, receptor positive breast cancer, or HER-2 positive breast cancer.

10. The method of claim 1 further comprising extracting an area in the tumor region along with the invasive edge around the tumor region and determining the recurrence of the disease based on the radiomics features in both the invasive edge and the tumor region area.

11. A system comprising:
a memory storing a machine learning model including a classifier and a deep learning network;
a display device; and
a processor communicably coupled to the memory and configured to:
receive a medical image of an organ of the patient;
rank a plurality of radiomics features based on their ability to predict the recurrence of the cancer using the classifier;
providing high ranking radiomics features of an invasive edge around an area of interest in the medical image to the deep learning network;
classify the medical image using the deep neural network as a disease recurrent image or a disease non-recurrent image based on the high ranking radiomics features; and display the disease recurrent image via the display device,
wherein the disease defines a breast cancer, and
wherein the deep neural network is trained on radiomics features that have been selected to predict the recurrence of the disease based on a plurality of training data pairs comprising noisy and pristine medical images.

12. The system of claim 11, wherein the processor is further configured to extract the invasive edge by segmenting the area of interest from the medical image.

13. The system of claim 11, wherein the invasive edge includes an edge surrounding the area of interest having a width.

14. The system of claim 13, wherein the width of the invasive edge is in the range of 0.5 mm to 1 cm.

15. The system of claim 11, wherein the plurality of radiomics features comprises shape, texture, intensity, and gradient magnitude of the invasive edge.

16. The system of claim 11, wherein the disease comprises triple negative breast cancer, receptor positive breast cancer, or HER-2 positive breast cancer.

* * * * *